United States Patent [19]

Strong

[11] 4,258,038
[45] Mar. 24, 1981

[54] UNSYMMETRICAL THIOPHOSPHONATE INSECTICIDES AND NEMATOCIDES

[75] Inventor: Jerry G. Strong, Midlothian, Va.

[73] Assignee: Mobil Oil Corporation, Fairfax, Va.

[21] Appl. No.: 71,464

[22] Filed: Aug. 31, 1979

[51] Int. Cl.³ .......................... A01N 57/12; C07F 9/40
[52] U.S. Cl. ...................................... 424/222; 260/961
[58] Field of Search ........................ 260/961; 424/222

[56] References Cited

U.S. PATENT DOCUMENTS

| | | | |
|---|---|---|---|
| 3,162,570 | 12/1964 | Wilson, Jr. | 424/163 |
| 3,209,020 | 9/1965 | Schrader | 260/961 |
| 3,705,216 | 12/1972 | Farley | 260/961 |

Primary Examiner—Anton H. Sutto
Attorney, Agent, or Firm—C. A. Huggett; M. G. Gilman; E. J. Trojnar

[57] ABSTRACT

Compounds of the formula

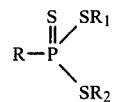

wherein R is alkyl of 1 to 6 carbon atoms; $R_1$ is an alkyl of 1 to 6 carbon atoms; and $R_2$ is branched alkyl of 3 to 8 carbon atoms. These compounds are insecticides and nematocides.

36 Claims, No Drawings

UNSYMMETRICAL THIOPHOSPHONATE INSECTICIDES AND NEMATOCIDES

CROSS-REFERENCE TO RELATED APPLICATION

An application entitled "BRANCHED-S-ALKYL PHOSPHONODITHIOIC HALIDE INTERMEDIATES AND PROCESS FOR THEIR PRODUCTION" filed on the same date as this application in the name of Mohamed G. Fahmy discloses certain intermediates useful for the production of insecticides and nematocides of this invention and the process for their preparation.

SUMMARY OF THE INVENTION

This invention relates to unsymmetrical thiophosphonate compounds and their use as insecticides and nematocides.

More particularly, the compounds of the invention have the formula

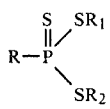

in which R alkyl of 1 to 6 carbon atoms; $R_1$ is alkyl of 1 to 6 carbon atoms; and $R_2$ is alkyl of 1 to 8 carbon atoms different from $R_1$.

Preferably, one of the members of $R_1$ and $R_2$ is branched alkyl.

These compounds exhibit a wide range of insecticidal activity and are of particular interest in controlling corn rootworm because of their excellent activity against this pest and their low phytotoxicity to corn plants.

DETAILED DESCRIPTION OF THE INVENTION

An important structural feature of the compounds of this invention is that they are unsymmetrical. Specifically, the characterization as "unsymmetrical" means that $R_1$ and $R_2$ in the formula above are different. Certain symmetrical thiophosphonate insecticides are broadly described in U.S. Pat. No. 3,162,570. Individual species described in the patent correspond to the above formula where R is methyl, and $R_1$ and $R_2$ are both n-propyl or are both n-butyl.

It has been found that the unsymmetrical compounds of this invention possess unexpected advantageous properties. In particular, they exhibit lower phytoxicity to corn than the corresponding symmetrical compounds. The symmetrical compounds have good activity against corn rootworm but are phytotoxic to corn. Since the activity of the unsymmetrical compounds against corn rootworm is as good or better than the symmetrical compounds and their phytotoxicity is less, the compounds of this invention are of special interest for controlling corn rootworm. Particularly good properties are obtained in compounds where $R_1$ and $R_2$ are different alkyl groups and at least one of the $R_1$ and $R_2$ is branched alkyl.

The compounds disclosed herein can be prepared by several methods. For instance, the reaction illustrated in Example 3, in which an alkylphosphonotrithioc anhydride is reacted with an alkyl thiol in the presence of a tertiary amine and the product is subsequently reacted with an alkyl halide, can be used.

Preferably, the compounds of this invention are prepared from a starting material which is a S-alkyl alkyl phosphonodithioic halide, the preparation of which is illustrated in Example 1. A more detailed description of the preparation of these starting materials is contained in an application by M. Fahmy, filed on the same date as this application, which application is incorporated herein by reference. The S-alkyl alkylphosphonodithioic halide is then reacted with an alkyl thiol in the presence of a base to arrive at the compounds of this invention. The preferred reaction scheme is as follows

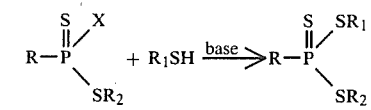

in which
R is alkyl of 1 to 6 carbon atoms;
$R_1$ is alkyl of 1 to 6 carbon atoms;
$R_2$ is alkyl of 1 to 8 carbon atoms and is preferably a branched alkyl of 3 to 8 carbon atoms; and
X is halogen, preferably Cl.

The reaction is advantageously carried out at a temperature of about 20° C. to 100° C. in an organic solvent in the presence of a tertiary amine, water or aqueous base, such as aqueous NaOh.

Suitable organic solvents are, for example, benzene, toluene, cyclohexane and 2-butanone.

Suitable tertiary amines include trimethyl amine, triethylamine, dimethyl aniline, diethyl aniline and pyridine.

The unsymmetrical thiophosphonate compounds of this invention are effective as insecticides and/or nematocides at low concentrations. Because of the small amounts of the compounds required for effective control, it is generally impractical to apply the compounds directly as such. Therefore, it is desirable that the compounds be applied in the form of liquid compositions, or in combination with other vehicles or extenders.

The compositions containing the active compounds of this invention can be dispersions or emulsions. Since the active compounds are substantially water insoluble, it is desirable to add a small amount of an inert, non-phytotoxic organic solvent which can be readily dispersed in an aqueous medium to produce a uniform dispersion of the active component. For example, an effective liquid composition can be prepared with the active component, acetone or ethanol, water, and a surface-active agent such as Tween-20 (polyoxyethylene sorbitan monolaurate) or any of the other well-known surface-active agents.

The compositions containing the active compounds can also be in powdered or granular form. For example, the active compound can be mixed with a suitable solid carrier such as kaolinite, bentonite, talc or the like, in amounts of about 5% to 20% by weight.

For the control of insects, the active ingredients are used at concentrations of from 0.01% to about 1% by weight of the total formulation. As nematocides, the active component is effective within the range of about 0.5 to 5 lbs/acre. Under ideal conditions, depending on the pest to be controlled, the lower rate may offer adequate protection. On the other hand, adverse weather conditions, resistence of the pest and other factors may require that the active ingredient be used in higher proportions.

When the pest is soil-borne, the formulation containing the active ingredient is distributed evenly over the area to be treated in any convenient manner. The active component can be washed into the soil by spraying with water over the area or can be left to the natural action of rainfall. After application, the formulation can be distributed in the soil by plowing or disking. Application can be prior to planting, after planting but before sprouting has taken place or after sprouting.

The following Examples illustrate the preparation of the compounds of this invention and their pesticidal properties. It will be understood that all of the compounds disclosed herein can be prepared by methods analogous to those described below. The homologues of the compounds described below wherein R is methyl instead of ethyl which have been prepared exhibit pesticidal properties similar to the ethyl compounds.

EXAMPLE 1

Preparation of S-tert.-butyl ethylphosphonodithioic chloride (Intermediate)

To a solution of ethylphosphonothioic dichloride (80 g, 0.5 mol) in 500 ml dry toluene, was added 2-methyl-2-propanethiol (50 g, 0.55 mol). The solution was stirred while triethylamine (60 g, 0.6 mol) was added dropwise. After the complete addition of the amine, the mixture was stirred and heated up to 80° C. for three hours and allowed to stand overnight. The reaction mixture was washed with 5% cold HCl solution (100 ml), followed by another wash with 5% cold NaOH solution (100 ml), finally washed twice with water (100 ml each), and dried over magnesium sulfate. Toluene was evaporated under a water aspirator vacuum, and the oil residue was distilled. The product distilled at 78°–80° C./0.2 mm. The yield was 60 g (55.4% of theoretical yield). The structure was confirmed by NMR.

EXAMPLE 2

Preparation of S-n-propyl S-tert.-butyl ethylphosphonotrithioate

To a solution of S-tert.-butyl ethylphosphonodithioic chloride (15 g, 0.07 mol) in 50 ml 2-butanone, was added 1-propanethiol (6.6 g, 0.09 mol), and triethylamine (10 g, 0.1 mol). The mixture was refluxed under nitrogen for three hours, then let stand at room temperature overnight. The amine hydrochloride was filtered and the solvent was evaporated under vacuum. Ether (100 ml) was added and the solution was washed with water (50 ml), followed by 5% NaOH solution (50 ml), then water (twice, 50 ml each). The ether solution was dried over anhydrous magnesium sulfate and the solvent was evaporated under vacuum. The residual oil was distilled to give the title compound b.p. 102°/0.4 mm. The product weighed 14.5 g (81% of theoretical yield). The structure was confirmed by NMR.

EXAMPLE 3

Preparation of S-n-Propyl S-iso-butyl Ethyl-phosphonotrithioate

To a 250 ml pressure bottle was added 6.2 g (0.025 mole) of ethylphosphonotrithioic anhydride [prepared from ethylphosphonothioic dichloride according to P. E. Newallis et. al *J. Org. Chem.* 27, 3829 (1962)], 4.5 g (0.05 mole) 2-methyl-1-propanethiol, 5.0 g (0.05 mole) of triethylamine and 50 ml benzene. The bottle was capped tightly and heated on the steam bath for 3 hours. Following cooling to room temperature, a 4.0 g (0.05 mole) portion of 1-chloropropane was added and the mixture again heated on the steam bath for 3 hours. The contents were cooled, filtered to remove hydrochloride salts, concentrated at the water pump and the residue distilled in a Kugelrohr (b.p. 105°130°/0.6 mm) to give 4.5 g after a small forerun. This structure was confirmed by NMR.

EXAMPLES 4–11

| Example | R | $R_1$ | $R_2$ |
| --- | --- | --- | --- |
| 4 | ethyl | n-propyl | iso-propyl |
| 5 | ethyl | n-propyl | n-butyl |
| 6 | ethyl | n-propyl | sec-butyl |
| 7 | ethyl | n-propyl | methyl |
| 8 | ethyl | n-propyl | ethyl |
| 9 | ethyl | ethyl | iso-propyl |
| 10 | ethyl | iso-propyl | iso-butyl |
| 11 | ethyl | n-propyl | iso-butyl |

EXAMPLE 12

Testing for corn rootworm intrinsic activity and for corn phytotoxicity.

A. Corn rootworm intrinsic activity

The test compound is prepared in a one percent solution with acetone or ethanol. The stock solution is then diluted with an aqueous solution of Tween 20 and water to the appropriate concentration (i.e., 100, 10, 1, 0.1, 0.01 ppm). Two ml of this solution is pipetted into a 9 cm. petri dish containing two layers of filter paper. Second instar larvae are introduced and the dish closed. Observations for mortality and moribund larvae are made after two days (48 days) exposure. Insecticidal activity is primarily contact and vapor action with minimum ingestion. The results are tabulated in TABLE I.

B. Corn phytotoxicity

Test compounds are dissolved in acetone to provide concentrations of 0.5 and 1.0% active ingredient. Corn seeds are planted in double rows in 9"×7" fiber flats containing pasteurized soil. Five seeds are planted in each furrow and lightly covered with soil. Treatment is made by applying 5 ml/row of test solution directly over the corn seed at the bottom of the furrow. The 0.5% and 1.0% solutions provide a rate of application equivalent to 1 and 2 lbs active ingredient/acre. After the furrows are closed, the flats are removed to the greenhouse, watered and held for observation and harvest. Three replicate flats are used for each treatment.

Assessment of corn tolerance after 8 days is made by by rating the response of individual plants on a 0–10 scale (where 0=no effect and 10=complete kill). Overall ratings are made for each replicate flat 2 weeks after treatment. Assessment of corn tolerance is also based on fresh weight of shoots that are harvested after the two week visual rating. The results are tabulated in Table 1.

TABLE I

| Compound Example | Corn Rootworm Activity Rate (PPM) | Corn Rootworm Activity % Kill | (lb/acre) | % Emergence | Corn Phytoxicity Phytoxicity Ratings By Plant (8 days) | Corn Phytoxicity Phytoxicity Ratings By Rep. (2 wks) |
|---|---|---|---|---|---|---|
| 2 | 1 | 100 | 1 | — | — | — |
|   | 0.1 | 100 | 2 | 90 | 1.6 | 0.6 |
|   | 0.01 | 45 |   |   |   |   |
|   | 0.005 | 10 |   |   |   |   |
| 3 | 1 | 100 | 1 | 100 | 0.2 | 0 |
|   | 0.1 | 50 | 2 | 80 | 1.3 | 1.0 |
| 4 | 1 | 95 | 1 | 63 | 0.3 | 1.0 |
|   | 0.5 | 100 | 2 | 87 | 1.8 | 1.3 |
|   | 0.1 | 65 |   |   |   |   |
| 5 | 1 | 100 | 1 | 87 | 0.1 | 0.3 |
|   | 0.1 | 40 | 2 | 97 | 1.9 | 0.6 |
| 6 | 1 | 100 | 1 | 57 | 0.2 | 1.0 |
|   | 0.1 | 95 | 2 | 73 | 2.0 | 1.6 |
| 7 | 1 | 100 | — | — | — | — |
|   | 0.1 | 30 | — | — | — | — |
|   | 0.01 | 0 | — | — | — | — |
| 8 | 1 | 100 | — | — | — | — |
|   | 0.1 | 100 | — | — | — | — |
|   | 0.01 | 10 | — | — | — | — |
| 10 | 1 | 95 | — | — | — | — |
|   | 0.1 | 65 | — | — | — | — |
| 11 | 1 | 100 | — | — | — | — |
|   | 0.1 | 85 | — | — | — | — |
|   | 0.01 | 0 | — | — | — | — |
| A* | 1 | 100 | 1 | 77 | 0.6 | 0 |
|   | 0.5 | 100 | 2 | 87 | 2.8 | 2.3 |
|   | 0.1 | 65 |   |   |   |   |
| B* | 1 | 100 | 1 | 67 | 0.9 | 1.0 |
|   | 0.1 | 85 | 2 | 83 | 3.2 | 2.3 |

Comparison compound A is a symmetrical compound in which R in the formula above is ethyl and each of $R_1$ and $R_2$ is n-propyl.

Comparison compound B is a symmetrical compound containing branching in which R in the formula above is ethyl and each of $R_1$ and $R_2$ is isopropyl.

I claim:

1. A method for controlling insects and nematodes which comprises applying thereto a pesticidal amount of a compound of the formula

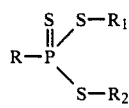

in which

R is an alkyl of 1 to 6 carbon atoms;
$R_1$ is an alkyl of 1 to 6 carbon atoms;
$R_2$ is a branched alkyl of 3 to 8 carbon atoms; and
$R_1$ and $R_2$ are different.

2. A method for controlling corn rootworm which comprises providing a pesticidal amount in the soil of a compound of the formula

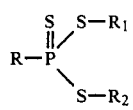

in which

R is an alkyl of 1 to 6 carbon atoms;
$R_1$ is an alkyl of 1 to 6 carbon atoms;
$R_2$ is a branched alkyl of 3 to 8 carbon atoms; and
$R_1$ and $R_2$ are different.

3. The method of claim 2 in which $R_1$ is unbranched alkyl of 1 to 6 carbon atoms.

4. The method of claim 2 in which $R_2$ is t-butyl.

5. The method of claim 2 in which R is methyl or ethyl.

6. The method of claim 2 in which R is methyl or ethyl;
$R_1$ is unbranched; and
$R_2$ is branched on the carbon atom bonded to S.

7. The method of claim 2 in which
R is ethyl;
$R_1$ is n-propyl; and
$R_2$ is isopropyl.

8. The method of claim 2 in which
R is ethyl;
$R_1$ is n-propyl; and
$R_2$ is t-butyl.

9. The method of claim 2 in which
R is ethyl;
$R_1$ is n-propyl; and
$R_2$ is isobutyl.

10. The method of claim 2 in which
R is ethyl;
$R_1$ is n-propyl; and
$R_2$ is sec-butyl.

11. The method of claim 2 in which
R is ethyl;
$R_1$ is ethyl; and
$R_2$ is isopropyl.

12. A composition comprising as the active ingredient a compound of the formula

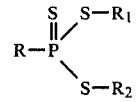

in which

R is an alkyl of 1 to 6 carbon atoms;
$R_1$ is an alkyl of 1 to 6 carbon atoms;
$R_2$ is a branched alkyl of 3 to 8 carbon atoms; and
$R_1$ and $R_2$ are different; in an amount effective as an insecticide or nematocide; and an inert, non-phytotoxic organic solvent or a solid carrier.

13. The composition of claim 12 in which $R_2$ is tertiary alkyl.

14. The composition of claim 12 in which $R_2$ is t-butyl.

15. The composition of claim 12 in which R is methyl or ethyl.

16. The composition of claim 12 in which R is methyl or ethyl;
$R_1$ is unbranched; and
$R_2$ is branched on the carbon atom bonded to S.

17. The composition of claim 12 in which
R is methyl or ethyl;
$R_1$ is unbranched; and
$R_2$ is tertiary alkyl.

18. The composition of claim 12 in which
R is methyl or ethyl;
$R_1$ is unbranched; and
$R_2$ is t-butyl.

19. The composition of claim 12 in which
R is ethyl;
$R_1$ is n-propyl; and
$R_2$ is isopropyl.

20. The composition of claim 12 in which
R is ethyl;
$R_1$ is n-propyl; and
$R_2$ is t-butyl.

21. The composition of claim 12 in which
R is ethyl;
$R_1$ is n-propyl; and
$R_2$ is isobutyl.
22. The composition of claim 12 in which
R is ethyl;
$R_1$ is n-propyl; and
$R_2$ is sec-butyl.
23. The composition of claim 12 in which
R is ethyl;
$R_1$ is ethyl; and
$R_2$ is isopropyl.
24. A compound of the formula

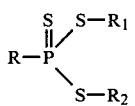

in which
R is an alkyl of 1 to 6 carbon atoms;
$R_1$ is an alkyl of 1 to 6 carbon atoms;
$R_2$ is a branched alkyl of 3 to 8 carbon atoms; and
$R_1$ and $R_2$ are different.
25. A compound of claim 24 in which $R_1$ is unbranched alkyl of 1 to 6 carbon atoms.
26. A compound of claim 24 in which $R_2$ is t-butyl.
27. A compound of claim 24 in which R is methyl or ethyl.
28. A compound of claim 24 in which R is methyl or ethyl;
$R_1$ is unbranched; and
$R_2$ is branched on the carbon atom bonded to S.
29. A compound of claim 24 in which
R is ethyl;
$R_1$ is n-propyl; and
$R_2$ is isopropyl.
30. A compound of claim 24 in which
R is ethyl;
$R_1$ is n-propyl; and
$R_2$ is t-butyl.
31. A compound of claim 24 in which
R is ethyl;
$R_1$ is n-propyl; and
$R_2$ is isobutyl.
32. A compound of claim 24 in which
R is ethyl;
$R_1$ is n-propyl; and
$R_2$ is sec-butyl.
33. A compound of claim 24 in which
R is ethyl;
$R_1$ is ethyl; and
$R_2$ is isopropyl.
34. A compound of claim 24 in which
$R_2$ is tertiary alkyl.
35. A compound of claim 24 in which
R is methyl or ethyl;
$R_1$ is unbranched; and
$R_2$ is tertiary alkyl.
36. A compound of claim 24 in which
R is methyl or ethyl;
$R_1$ is unbranched, and
$R_2$ is t-butyl.

* * * * *